United States Patent
White et al.

(10) Patent No.: US 8,806,915 B2
(45) Date of Patent: Aug. 19, 2014

(54) MICROFABRICATED PARTICULATE MATTER MONITOR

(75) Inventors: Richard M. White, Berkeley, CA (US); Igor Paprotny, Berkeley, CA (US); Frederick Doering, Hayward, CA (US)

(73) Assignee: University of California, Berkeley, CA (US)

( * ) Notice: Subject to any disclaimer, the term of this patent is extended or adjusted under 35 U.S.C. 154(b) by 245 days.

(21) Appl. No.: 13/205,313

(22) Filed: Aug. 8, 2011

(65) Prior Publication Data

US 2013/0036793 A1    Feb. 14, 2013

(51) Int. Cl.
*G01N 21/00*    (2006.01)

(52) U.S. Cl.
USPC .......................................... 73/24.02

(58) Field of Classification Search
USPC .......................................... 73/865.5
See application file for complete search history.

(56) References Cited

U.S. PATENT DOCUMENTS

| | | | | |
|---|---|---|---|---|
| 5,607,497 A | * | 3/1997 | Brown | 73/864.71 |
| 5,616,872 A | * | 4/1997 | O'Brien | 73/865.5 |
| 2010/0288043 A1 | * | 11/2010 | Manalis et al. | 73/32 R |

* cited by examiner

*Primary Examiner* — Peter Macchiarolo
*Assistant Examiner* — Alex Devito
(74) *Attorney, Agent, or Firm* — David R. Stevens; Stevens Law Group (57) ABSTRACT

An apparatus for measuring concentrations of airborne particulate matter may include, in one embodiment, a primary channel to receive air samples from the external environment. The air samples include particles of varying sizes. A microfluidic circuit communicates with the primary channel and small particles (having a size less than a threshold size) are diverted around a bend into a secondary channel. Remaining larger particles are unable to make the bend and continue through the primary channel. A mass-sensitive element communicating with the secondary channel includes a collection surface to collect the small particles. A resonant frequency of the mass-sensitive element is reduced in proportion to the mass of the particles collected.

18 Claims, 8 Drawing Sheets

MICROFABRICATED PARTICULATE MATTER MONITOR

BACKGROUND

This invention relates to particulate matter sensors, and particularly to microfabricated particulate matter sensors to measure concentrations of micron-sized particulate matter in the atmosphere.

Airborne particulate matter ("PM") pollutants are small solid particles or liquid droplets suspended in the atmosphere. These may include, for example, diesel exhaust, tobacco smoke, volcanic ash, and pollen. PM pollutants have diameters ranging from many tens of microns down to a few nanometers. PM pollutants measuring 2.5 microns in diameter or less ($PM_{2.5}$), or finer particles, are particularly harmful to humans as they may penetrate deep into respiratory systems, and may even get into the bloodstream. In fact, studies show a connection between PM and respiratory and cardiac problems such as aggravated asthma, irregular heartbeat, and premature death in people with reduced heart or lung functionality.

The United States Environmental Protection Agency ("EPA") sets standards for $PM_{2.5}$ concentrations in urban air. The EPA has recently reduced its acceptable 24-hour concentration exposure limit for individuals to 35 micrograms/$m^3$. This exposure limit, however, is based on sparse data obtained from large stationary measurement stations. Indeed, existing PM monitors used to measure PM concentration tend to be expensive and have large footprints, rendering them unable to provide detailed measurement information relevant to personal PM exposure at varied locations. While several small-sized PM monitors have recently been developed, these are still too large to allow large-scale deployment as personal PM monitors.

Further, existing PM monitors are generally unable to simultaneously measure multiple PM characteristics, such as PM mass, particle size distributions, chemical composition, and optical properties, to enable accurate identification of PM emissions sources. This identifying information may be used to facilitate strategic targeting of emission reduction approaches, as well as to increase individual awareness of areas or situations likely to aggravate certain medical conditions. Even if this information were currently available, however, it may be inaccurate since existing PM monitors are generally fixed at a few permanent locations.

In view of the foregoing, what are needed are apparatus and methods to reliably measure concentrations of airborne particulate matter at widely varied locations. Further what are needed are apparatus and methods for monitoring airborne particulate matter that are small, inexpensive to manufacture, and easy to carry and utilize. Such apparatus and methods are disclosed and claimed herein.

BRIEF DESCRIPTION OF THE DRAWINGS

In order that the advantages of the invention will be readily understood, a more particular description of the invention briefly described above will be rendered by reference to specific examples illustrated in the appended drawings. Understanding that these drawings depict only typical examples of the invention and are not therefore to be considered limiting of its scope, the invention will be described and explained with additional specificity and detail through the use of the accompanying drawings, in which.

DETAILED DESCRIPTION

The invention has been developed in response to the present state of the art, and in particular, in response to the problems and needs in the art that have not yet been fully solved by currently available methods and apparatus for measuring concentrations of airborne particulate matter. Accordingly, the invention has been developed to provide a novel apparatus, system and method for collecting and monitoring concentrations of micron-size airborne particulate matter. The features and advantages of the invention will become more fully apparent from the following description and appended claims and their equivalents, and also any subsequent claims or amendments presented, or may be learned by practice of the invention as set forth hereinafter.

In one embodiment, an apparatus for measuring concentrations of airborne particulate matter includes a primary channel to receive air samples from the external environment. The air samples may include particles of varying sizes. A microfluidic circuit communicates with the primary channel and small particles (having a size less than a threshold size) are diverted around a bend into a secondary channel. Remaining larger particles that are unable to make the bend continue through the primary channel. A mass-sensitive element communicating with the secondary channel includes a collection surface to collect the small particles. A resonant frequency of the mass-sensitive element is reduced in proportion to the mass of the particles collected.

In another embodiment, a method for measuring concentrations of airborne particulate matter includes drawing air samples into a primary channel from an external environment. The air samples include particles of various sizes. Particles having a size less than a threshold size are diverted around a bend into a secondary channel. Remaining particles having a size larger than the threshold size and unable to make the bend continue through the primary channel. The particles having a size less than the threshold size are collected onto a mass-sensitive element, such that a resonant frequency of the mass-sensitive element is reduced in proportion to the mass of the particles collected.

It will be readily understood that the components of the present invention, as generally described and illustrated in the Figures herein, could be arranged and designed in a wide variety of different configurations. Thus, the following more detailed description of the embodiments of apparatus and methods in accordance with the present invention, as represented in the Figures, is not intended to limit the scope of the invention, as claimed, but is merely representative of certain examples of presently contemplated embodiments in accordance with the invention. The presently described embodiments will be best understood by reference to the drawings, wherein like parts are designated by like numerals throughout.

As used herein, the term "size" and the term "aerodynamic diameter" are used substantially interchangeably to refer to the diameter of a spherical particle with a density of 1000 kg/m$^3$ that has the same settling velocity in air as the aerosol particle. The term "optical" refers to any form of electromagnetic radiation such as visible light, infrared illumination, radio-frequency radiation, ultraviolet light, and the like.

Figure 1:
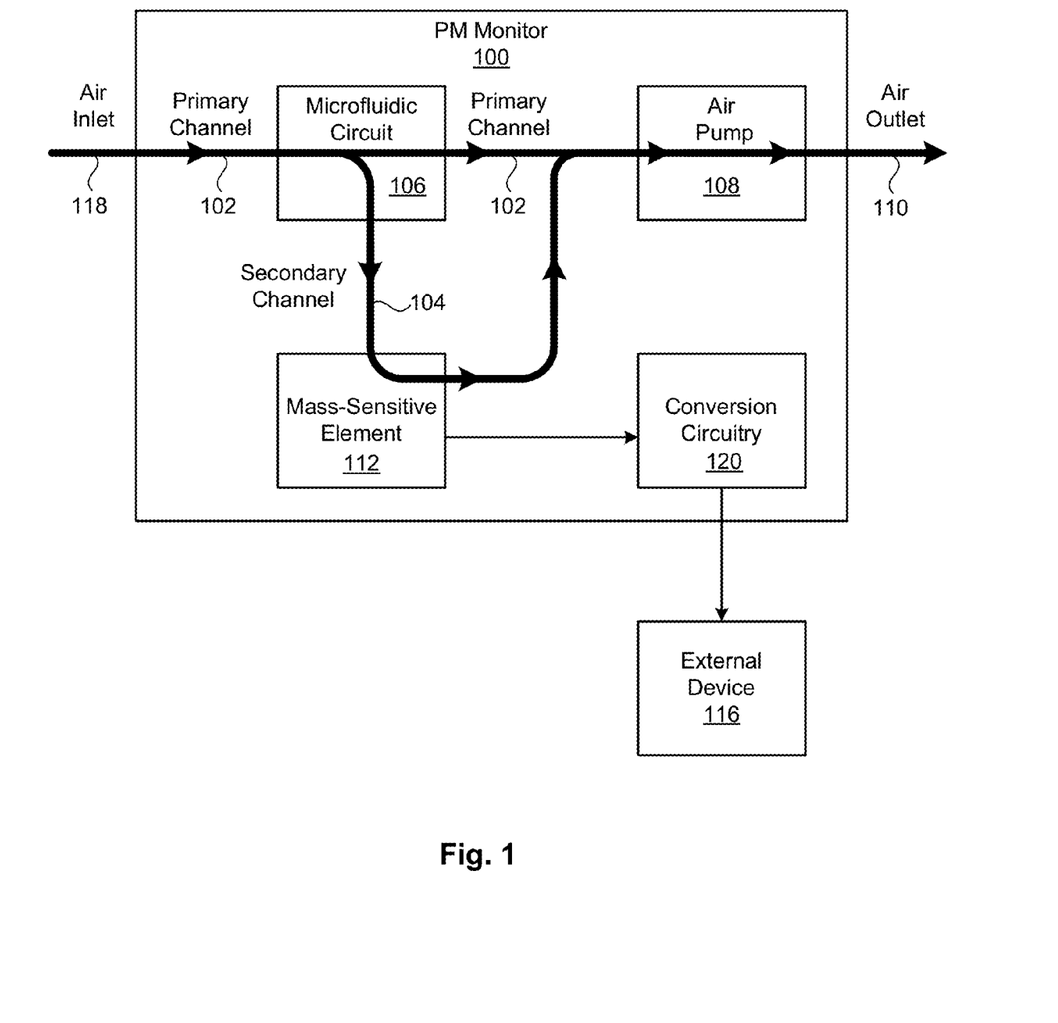
FIG. 1 is a block diagram of one embodiment of a PM monitor in accordance with the present invention.

With reference now to FIG. 1, an apparatus or particulate matter ("PM") monitor 100 for measuring concentrations of airborne particulate matter in accordance with embodiments of the invention may draw air samples 118 from the external environment, and utilize inertial forces to filter and measure concentrations of micron-sized particulate matter contained therein. Such particulate matter may include, for example, diesel exhaust particles, tobacco smoke, volcanic ash, and airborne particles to which humans are often allergic, such as pollen and foodstuffs. To this end, the PM monitor 100 may include an air pump 108, a microfluidic circuit 106, and a mass-sensitive element 112. The PM monitor 100 may also include a power source, such as a battery, to power the air pump 108 and/or any other internal or co-located components.

The air pump 108 may create a pressure gradient across the microfluidic circuit 106 to draw air samples 118 into the primary channel 102, through the microfluidic circuit 106, and ultimately out of the apparatus via an air outlet 110. The air pump 108 may produce a sufficient pressure gradient to overcome the pressure loss of the microfluidic circuit 106 at a desired flow rate. In one embodiment, for example, the air pump 108 may produce about 55 Pa of negative pressure across the microfluidic circuit 106 to achieve an air sample 100 flow rate of about $1.0 \times 10^{-7}$ m$^3$/s.

Initially, air samples 118 may be drawn into a primary channel 102 communicating with the microfluidic circuit 106. As discussed in more detail below, the microfluidic circuit 106 may include one or more secondary channels 104 contoured to separate the air samples 118 into two or more airstreams, based on the size (aerodynamic diameters) of particles contained therein.

In one embodiment, for example, particles having a size less than a threshold size (such as 2.5 microns, for example) are diverted around a bend into a secondary channel 104 communicating with the primary channel 102. Remaining particles are unable to make the bend and continue through the primary channel 102. Thus, in certain embodiments, an air stream corresponding to the secondary channel 104 may contain particles having aerodynamic diameters of 2.5 microns or less, while the air stream corresponding to the primary channel 102 may contain particles having aerodynamic diameters greater than 2.5 microns.

As discussed in more detail below with reference to FIGS. 2a and 2b, the secondary channel 104 may include a collection region where particles having a size less than a threshold size may be deposited onto a mass-sensitive element 112 to measure the mass concentration of the particles. The mass-sensitive element 112 may be, for example, a piezoelectric crystal such as a Film Bulk Acoustic Resonator ("FBAR").

The mass-sensitive element 112 may be used to determine mass concentration of the collected particles because its oscillation frequency decreases in proportion to the mass of particles that reach and adhere to it. Before particles are collected onto it, the mass-sensitive element 112 may oscillate within a substantially high frequency range (i.e., around 1.6 GHz). As particles are deposited onto the mass-sensitive element 112, the frequency at which it oscillates may decrease proportionally. In certain embodiments, after long-term use, the mass-sensitive element 112 may be strongly driven to shake off some or most of the collected particles to permit in situ renewal of its sensing ability.

In some embodiments, the mass-sensitive element 112 may be connected to solid-state conversion circuitry 120. Such conversion circuitry 120 may measure the changing frequency of the mass-sensitive element 112 as particles are deposited onto it. Based on this measurement, mass concentration of the sampled particles may be determined. For example, in one embodiment, the conversion circuitry 120 includes a high-speed frequency counter to determine the rate of frequency shift of the mass-sensitive element 112. In other embodiments, the conversion circuitry 120 may include a reference fixed-frequency oscillator and an RF mixer circuit, for example, to convert the rate of change from a high frequency (i.e., around 600 MHz) to a lower value (i.e., around 10 MHz), where measuring the rate of change of oscillator frequency may be accomplished more easily. The mass concentration of the particles may be determined based on the rate at which the frequency of the mass-sensitive element 112 is reduced.

A wireless device (not shown) may be attached to or integrated with the conversion circuitry 120 to wirelessly communicate the mass concentration measurement data to an external device 116 for analysis. In one embodiment, RF signals generated by the conversion circuitry 120 may be transmitted to the external device 116 by way of a wireless device such as an antenna, radio mote, or the like.

Figure 2A:
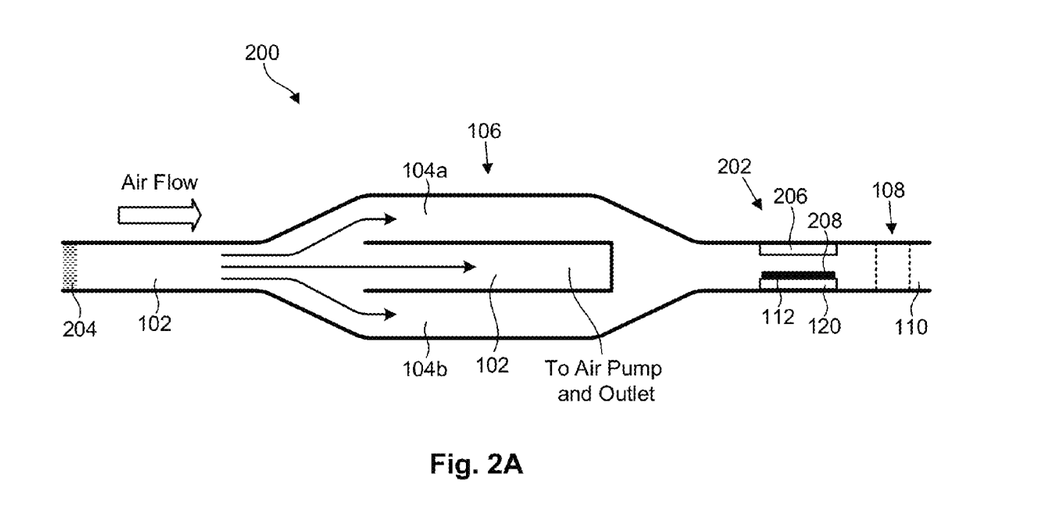
FIG. 2a is a high-level schematic of a PM monitor in accordance with one embodiment of the invention.
Figure 2B:
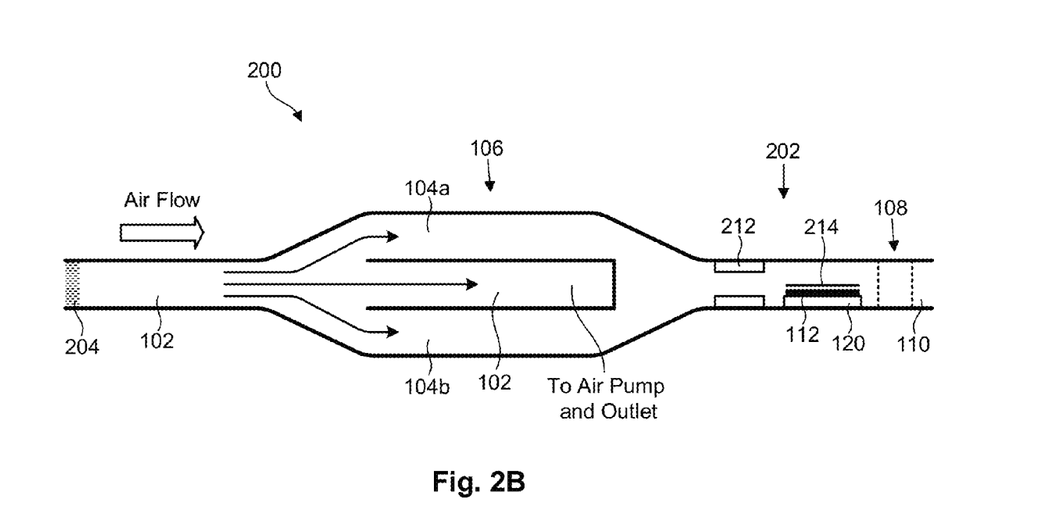
FIG. 2b is a high-level schematic of a PM monitor in accordance with an alternative embodiment of the invention.

FIGS. 2a and 2b illustrate exemplary embodiments of a PM monitor 100 in accordance with the invention. As shown, certain embodiments of the PM monitor 100 may include an air inlet 204 to receive air samples 118 into the PM monitor 100 from the ambient environment. Optionally, the air inlet 204 may include a coarse filter to prevent large particulates from entering the PM monitor 100.

After being received into the air inlet 204, air samples 118 may proceed through the primary channel 102 and microfluidic circuit 106. As previously mentioned, the microfluidic circuit 106 may utilize inertial forces to further filter particulate matter contained in the air samples 118 according to size. Specifically, the primary channel 102 may branch into one or more secondary channels 104 angled away from the primary channel 102. The angle at which the secondary channels 104 branch from the primary channel 102 may be selected such that only small particles (having a size or aerodynamic diameter below a threshold size) may make the bend and be received into the secondary channels 104.

In some embodiments, remaining larger particles may continue through the primary channel 102 for exhaustion via an air outlet 110. In other embodiments, as discussed in more detail below, the larger particles may be collected and measured prior to exiting the PM monitor 100. In still other embodiments, air samples 118 may bypass the microfluidic circuit 106 completely and proceed directly to the mass-sensitive element 112 to enable measurement of total suspended particles ("TSP").

One or more mass-sensitive elements 112, such as piezoelectric crystals or FBARs, may communicate with each or all secondary channels 104. In certain embodiments, a mass-sensitive element 112 may include a collection surface 208 having a shape and characteristics to attract and retain small particles suspended in the air samples 118.

For example, in some embodiments, particles may adhere to the collection surface 208 as a result of van der Waals force. In other embodiments, the collection surface 208 may be treated with a sticky substance, or may be made of a material having adhesive or absorptive properties. In one embodiment, for example, the collection surface 208 may be coated with densely distributed structures, such as nanowires or nanotubes, configured such that particles become trapped in interstices of the structures.

Certain embodiments of the PM monitor 100 may include a deposition element 202 to facilitate deposition of airborne particles onto the collection surface 208. For example, as shown in FIG. 2a, the deposition element 202 is a thermophoretic heater 206 that produces a thermophoretic force to deflect particles toward the collection surface 208. The thermophoretic heater 206 may be, for example, a heated plate situated across from, or otherwise in proximity to, the collection surface 208. In other embodiments, the thermophoretic heater 206 may be a wire, a series of wires, a substrate with a conductive coating, or any other suitable material known to those in the art. In such embodiments, the mass-sensitive element 112 may be thermally compensated to reduce its dependence upon temperature.

As shown in FIG. 2b, another embodiment of a deposition element 202 may include an ionizer 212 and electret 214. In such an embodiment, air samples 118 may be passed through the ionizer 212 such that particles in the airstream become electrically charged. In one embodiment, the ionizer 212 may include a plurality of conducting nanowires fabricated on a planar conducting surface at right angles relative thereto. This conducting plate may be placed opposite and in close proximity (i.e., within about 100 microns) to a second conducting plate. When a potential is applied between the two plates, a corona discharge may take place in the intervening space, causing particles passing through the region to become electrically charged.

The mass-sensitive element 112 may be composed of, coated with, or otherwise associated with an insulator into which electric charges have been driven, known as an electret 214. The electret 214 may work in conjunction with the ionizer 212, such that charged particles in the airstream may be attracted to the electret 214 and associated mass-sensitive element 112. Alternatively, in some embodiments, the charged particles may be deflected towards the mass-sensitive element 112 with an applied voltage from an external supply.

In other embodiments, the deposition element 202 may include only an electret 214 associated with the mass-sensitive element 112. For example, airborne pollen is often electrically charged in nature. As a result, a PM monitor 100 designed to monitor natural pollen may rely on the existing electrical charge of the pollen to attract pollen particles to the electret 214, without requiring implementation of the ionizer 212 in conjunction therewith.

In any event, as particles are deposited onto the collection surface 208 of the mass-sensitive element 112, mechanical loading reduces the natural resonant frequency of the mass-sensitive element 112. In other words, the mass-sensitive element 112 resonates at progressively lower frequencies as mass is added to it. This reduction in resonant frequency is proportional to the fractional increase in mass of the mass-sensitive element 112. Conversion circuitry 120 connected to or communicating with the mass-sensitive element 112 may measure the rate of decrease of the resonant frequency of the mass-sensitive element 112 and convert that rate to mass concentration per unit volume of sampled air 118.

Figure 3:
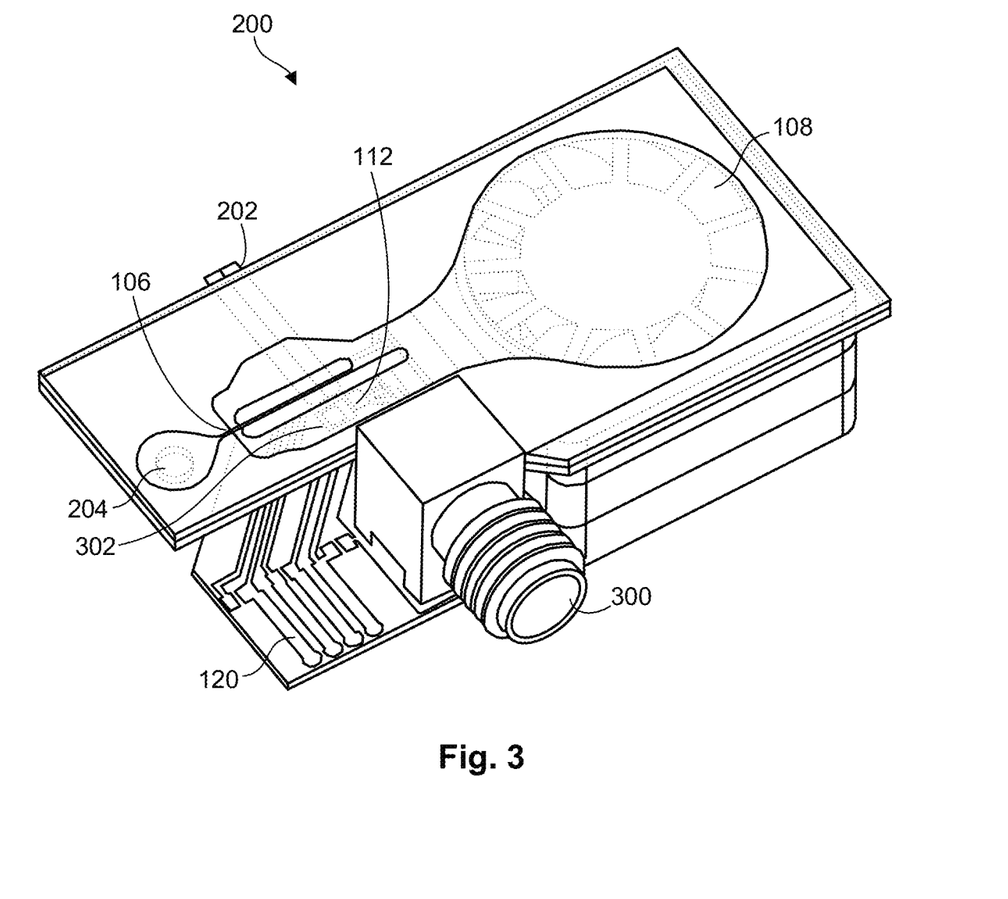
FIG. 3 is a perspective view of a PM monitor in accordance with certain embodiments of the invention.
Figure 4:
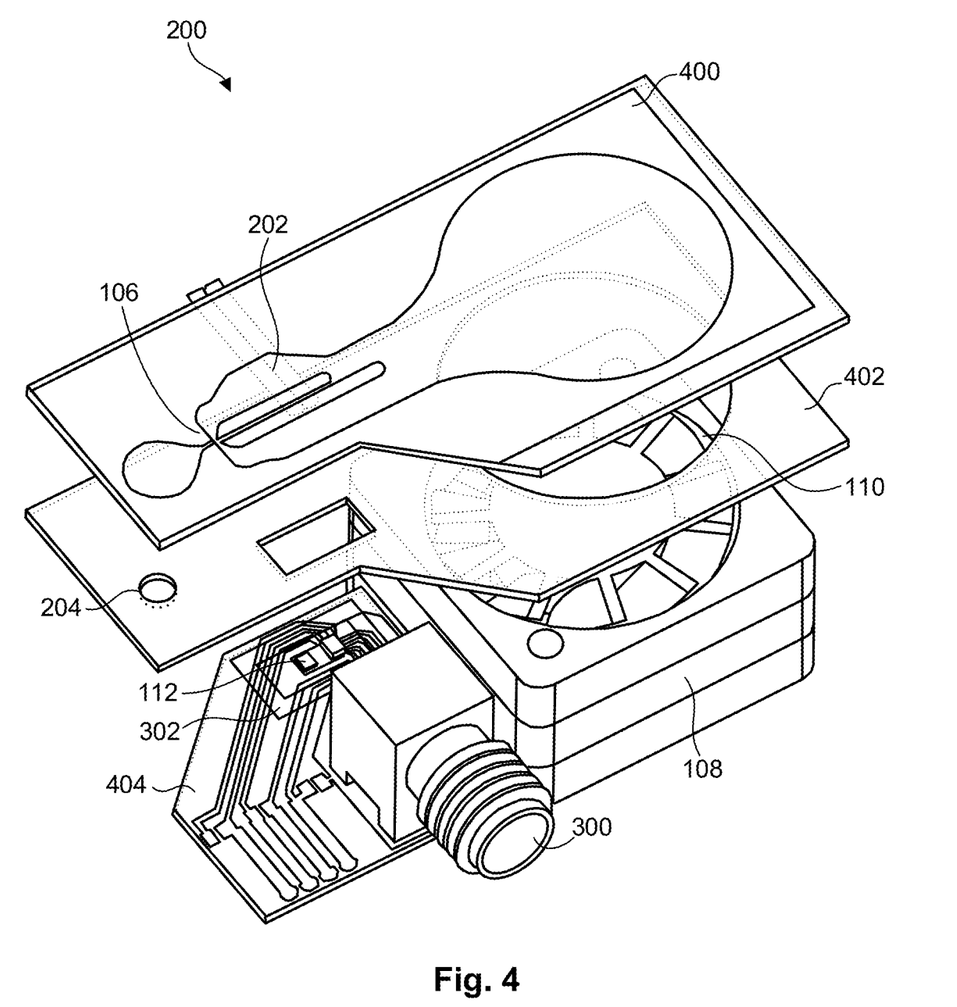
FIG. 4 is an exploded view of the PM monitor of FIG. 3.
Figure 8A:
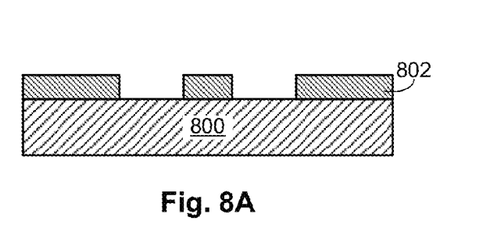
FIGS. 8a-8f are schematic diagrams illustrating an exemplary fabrication process for making a PM monitor in accordance with the present invention.

FIGS. 3 and 4 illustrate one embodiment of a PM monitor 100 in accordance with the present invention. As shown, and as described in more detail with reference to FIG. 8 below, the PM monitor 100 may be fabricated using a triple fused quartz wafer stack into which ports may be etched or drilled, and on which other elements, such as a thermophoretic heater 206 and conversion circuitry 120, may be fabricated.

For example, the bottom wafer 404 may contain the mass-sensitive element 112 and conversion circuitry 120, such as a CMOS oscillator circuit. In one embodiment, the mass-sensitive element 112 and conversion circuitry 120 may be assembled in a self-contained package that may be later installed in the PM monitor 100 to reduce the complexity and cost of initial manufacture. This assembly may also facilitate replacement of the mass-sensitive element 112 to renew its mass-sensing capability after long-term use.

The bottom wafer 404 may also contain a seal 302, made of SU-8 for example, to ensure that no air leaks out of the microfluidic circuit 106. In some embodiments, an RF coaxial connector 300 may be attached to or integrated with the bottom wafer 404 to enable an RF signal carrying mass concentration measurement data to be communicated to an external device 116 for interpretation and analysis.

The middle wafer 402 may contain airflow inlet 204 and outlet 110 holes, as well as a cavity through which the mass-sensitive element 112 of the bottom wafer 404 may be inserted to communicate with the microfluidic circuit 106.

The top wafer 400 may contain the microfluidic circuit 106 and, in some embodiments, a thermophoretic heater 206. As discussed above, the microfluidic circuit 106 may include a primary channel 102 communicating with an airflow inlet 204, and one or more secondary channels 104 extending at an angle from the primary channel 102. The mass-sensitive element 112 may be situated to communicate with the secondary channel 104 such that small particles able to make the bend in the secondary channel 104 may be collected onto a collection surface 208 thereof.

In certain embodiments, the microfluidic circuit 106 may be designed to select particulate matter having an aerodynamic diameter of 2.5 microns or less ($PM_{2.5}$) for deposition onto the collection surface 208 of the mass-sensitive element 112. This aerodynamic diameter may be selected to match the EPA standard. Particles smaller than 2.5 microns may be carried in the major flow (corresponding to the secondary channel 104), while larger particles may be exhausted via the minor flow (corresponding to the primary channel 102). As discussed above, the secondary channel 104 may route $PM_{2.5}$ to the mass-sensitive element 112 for collection and analysis.

In one embodiment, the microfluidic circuit 106 may include channels 102, 104 having a rectangular cross-sections for ease of manufacturing. One skilled in the art will recognize, however, that the invention is not so limited, and that primary and secondary channels 102, 104 may be fabricated to include any cross-sectional shape known to those in the art.

In some embodiments, a thermophoretic heater 206 may be fabricated such that the thermophoretic heater 206 is situated substantially opposite the mass-sensitive element 112 when the wafers 400, 402, 404 are assembled. As previously mentioned, the thermophoretic heater 206 may facilitate deposition of particles onto the collection surface 208 of the mass-sensitive element 112 by creating a localized temperature gradient. The temperature gradient may precipitate particles from the secondary channel 104 onto the collection surface 208.

Thermophoretic deposition of particles onto the collection surface 208 may be approximated analytically. To approximate the effect of the thermal force on the particles, it may be assumed that the thermal force acts only in the space between the thermophoretic heater 206 and the collection surface 208, and that the thermal gradient is uniform in this region. Under these conditions, the thermal force on the particles ($F_{th}$) is normal to the collection surface 208 and is approximated by:

$$F_{th} = \frac{-9 \cdot \pi \cdot d \cdot \eta^2 \cdot H \cdot \nabla T}{2 \cdot \rho_g \cdot T}$$

where d is the particle diameter, $\eta$ is the dynamic viscosity of the gas, $\nabla T$ is the temperature gradient, $\rho_g$ is the density of the gas, T is the absolute temperature of the gas, and H is the molecular accommodation coefficient. H is defined as:

$$H \cong \left(\frac{1}{1+6\lambda/d}\right)\left(\frac{k_a/k_p + 4.4\lambda/d}{1 + 2k_a/k_p + 8.8\lambda/d}\right)$$

where $k_a$ and $k_p$, are the thermal conductivities of air and the particle, respectively, and $\lambda$ is the mean free path length of the gas. The absolute temperature T is approximated as the average of the temperatures of the thermophoretic heater 206 and the collection surface 208, which yields a constant thermal force in the region between the thermophoretic heater 206 and the collection surface 208. Equating this force with the Stokes drag force yields a thermal particle velocity according to the following equation:

$$V_{th} = \frac{-3 \cdot \eta \cdot C_c \cdot H \cdot \nabla T}{2 \cdot \rho_g \cdot T}$$

where $C_c$ is the Cunningham correction factor:

$$C_c = 1 + \frac{2.52\lambda}{d}$$

In one example, the predicted thermal velocity equals 1.36 mm/s. Assuming the airflow replenishes particles significantly faster than they are deposited, the mass deposition rate is:

$$M_d = A_d \cdot V_{th} \cdot C$$

where $A_d$ is the area of deposition and C is the mass concentration of particles.

The figure of merit for the application of concentration detection is the ratio of mass deposition rate to particle concentration. Accordingly, it may be advantageous to minimize the distance between the thermophoretic heater 206 and the collection surface 208, maximize the heater 206 temperature, and minimize the collection surface 208 temperature. As discussed in more detail below, the airflow velocity may have no effect on the deposition rate so long as it remains significantly higher than the thermal velocity.

Figure 5:
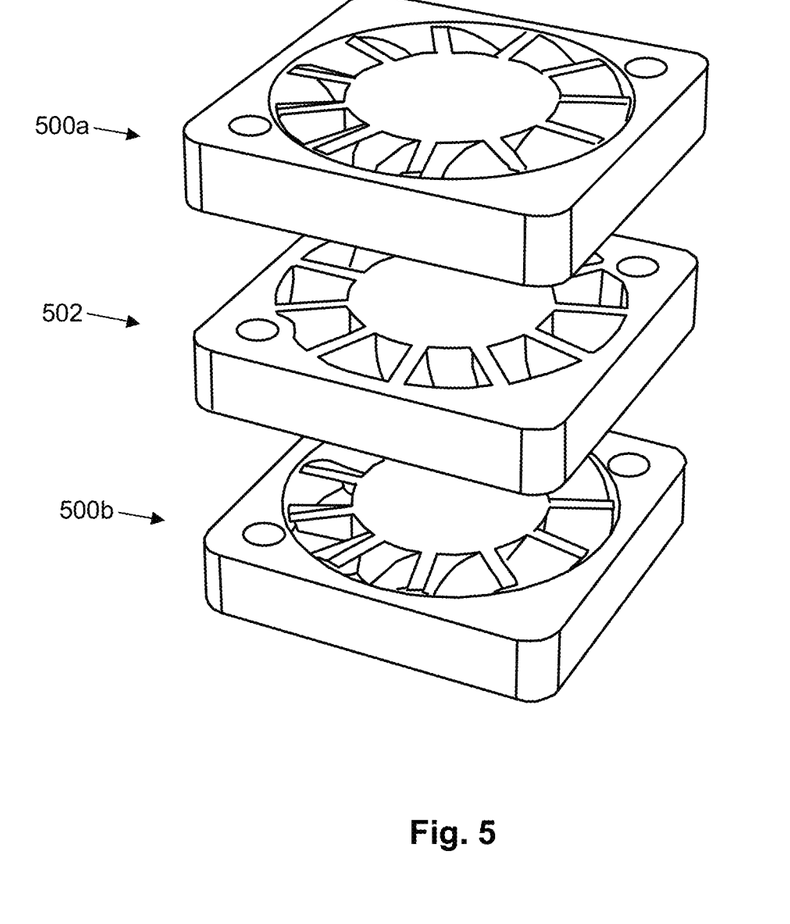
FIG. 5 is an exploded view of an air pump that may be used in connection with embodiments of the present invention.

Referring now to FIG. 5, the air pump 108 may communicate with the microfluidic circuit 106 (including the primary channel 102 and secondary channels 104a, 104b) to produce a pressure gradient to draw air samples 118 from the external environment therethrough. As mentioned above with reference to FIGS. 3 and 4, in some embodiments, the air pump 108 may be situated beneath the air outlet 110 and may communicate with the microfluidic circuit 106 to draw air samples 118 therethrough. The pressure gradient created by the air pump 108 must be sufficient to overcome the pressure loss of the microfluidic circuit 106 at the desired flow rate.

In one embodiment, the air pump 108 includes two small fans 500a, 500b stacked with a stator 502 of the opposite chirality between them. The stator 502 may convert the parasitic rotational momentum of the fans 500a, 500b into additional pressure, thereby increasing the overall efficiency of the air pump 108. Of course, one skilled in the art will recognize that any number of fans 500 and stators 502 may be utilized in any configuration to achieve the desired flow rate.

Although it is not initially obvious, once the PM monitor 100 has been calibrated (i.e., the rate of frequency reduction of the mass-sensitive element 112 has been determined with a test sample whose mass concentration is known), the speed of the air pump 108 may be varied to adjust the size range of particles selected by the microfluidic circuit 106. Accordingly, some embodiments of the present invention include a variable-speed air pump 108 to enable the PM monitor 100 to be customized for collection of particles falling within a predefined, variable size range.

Figure 6:
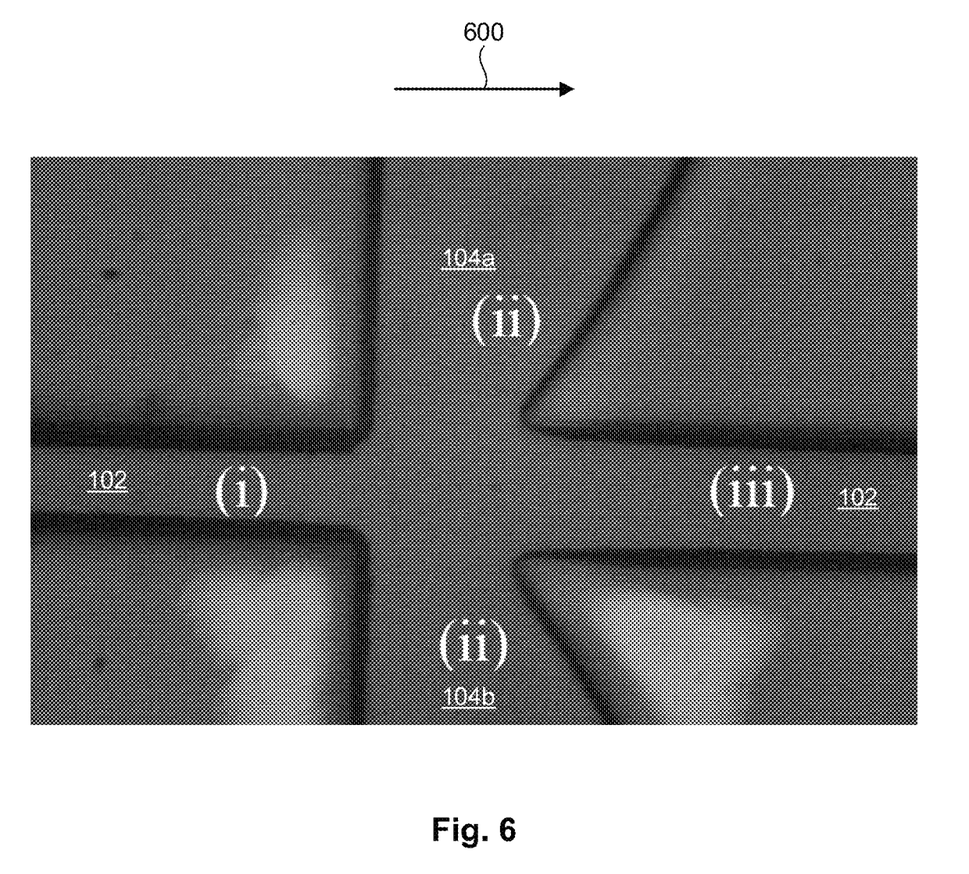
FIG. 6 is an optical micrograph of a microfluidic circuit of one embodiment of a PM monitor.

FIG. 6 is an optical micrograph illustrating one embodiment of a microfluidic circuit 106 in accordance with the invention. As shown, the microfluidic circuit 106 includes a primary channel 102 and secondary channels 104a, 104b extending substantially perpendicularly from the primary channel 102. One skilled in the art will recognize, however, that a right angle between the primary channel 102 and the secondary channels 104a, 104b is not required, and that the secondary channels 104a, 104b may be contoured to diverge from the primary channel 102 at any suitable angle or direction known to those in the art.

In operation, air samples 118 proceed in a direction 600 from the air inlet 204 to the air outlet 110, and from the primary channel 102 to the secondary channels 104a, 104b, propelled by the pressure gradient produced by the air pump 108. As discussed above, the forward movement 600 of the air samples 118 combined with the angles at which the secondary channels 104a, 104b branch from the primary channel 102 effectively strip smaller particles from the initial air stream and toward the mass-sensitive element 112. Particles above a certain size possess so much momentum that they cannot follow the divergent secondary channels 104a, 104b, and remain in the primary channel 102 for exhaustion from the PM monitor 100 or for separate collection and analysis.

Indeed, in certain embodiments, another mass-sensitive element 112 may communicate with the primary channel 102 at a location downstream from the point at which the secondary channels 104a, 104b branch from the primary channel 102. In this manner, larger particles remaining in the primary channel 102 airstream may be separately collected and analyzed.

The equation governing particle cutoff diameter (i.e., the aerodynamic diameter at which half of the particles follow the major flow corresponding to the secondary channels 104a, 104b) is:

$$d_{50} = \left(\frac{9\eta W^2 D(Stk_{50})}{\rho_p Q}\right)^{\frac{1}{2}}$$

where $d_{50}$ is the particle cutoff diameter, $\eta$ is the dynamic viscosity of air, W and D are the width and depth of the channel respectively, $\rho_p$ is the particle density, Q is the channel volumetric flow rate, and $Stk_{50}$ is the Stokes number (which may be 0.59 for microfluidic circuits 106 having rectangular channels 102, 104). Estimation of the pressure drop across the microfluidic circuit 106 may be obtained by summing the viscous losses according to the following equation:

$$\Delta P_v = 32 \eta v_{ave} \frac{L}{D_H}$$

where $\Delta P_v$ is the pressure loss due to viscous effects, $v_{ave}$ is the average velocity, L is the length of the channel, and $D_H$ is the hydraulic diameter of the channel, with the mixing losses defined as:

$$\Delta P_m = \frac{1}{2} \rho_g v_{ave}^2$$

where $\Delta P_m$ is the pressure loss due to mixing losses, $\rho_g$ is the density of air, and $v_{ave}$ is the average velocity.

As evidenced by the foregoing equations, reducing the width of the channel 102, 104 while keeping the particle cutoff diameter constant reduces pressure loss and required flow rate. In certain embodiments, a channel 102, 104 may include a width and depth of about 200 μm to minimize pressure loss and required flow rate, while enabling larger particles to pass through without clogging.

Figure 7A:
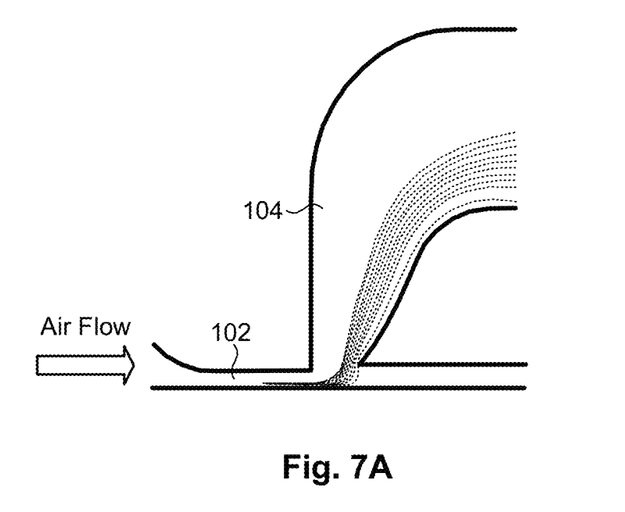
FIG. 7a is a graph of particle trajectories through the microfluidic circuit calculated for particles having aerodynamic diameters of about 0.5 µm.
Figure 7B:
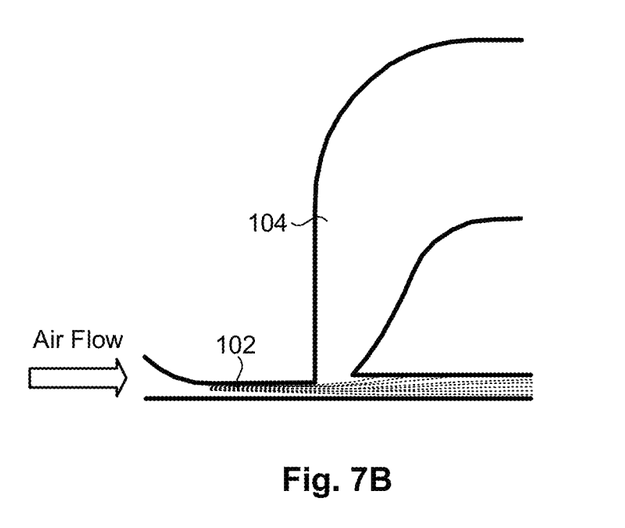
FIG. 7b is a graph of particle trajectories through the microfluidic circuit calculated for particles having aerodynamic diameters of about 5 µm.

FIGS. 7a and 7b illustrate the calculated fractional transmission through the microfluidic circuit 106 versus aerodynamic particle diameter. Specifically, FIG. 7a shows the calculated trajectories through the microfluidic circuit 106 for particles having an aerodynamic diameter of 0.5 μm. FIG. 7b shows the calculated trajectories through the microfluidic circuit 106 for particles having an aerodynamic diameter of 5 μm.

As shown in FIG. 7a, small particles having an aerodynamic diameter of 0.5 μm are initially received into the primary channel 102 along with other larger particles in the air samples 118. Upon encountering the secondary channel 104, nearly all of the small particles are able to make the bend defining the secondary channel 104, and thus diverge from the primary channel 102 to follow the secondary channel 104.

On the other hand, as shown in FIG. 7b, large particles having an aerodynamic diameter of 5 μm are not able to make the bend defining the secondary channel 104. Initially, the large particles, like the small particles, are received into the primary channel 102. Because of the angle at which the secondary channel 104 extends from the primary channel 102, however, almost no large particles are able to make the bend, and instead continue to follow the primary channel 102. In this manner, small particles are effectively stripped from the initial airstream, thereby substantially maximizing the collection efficiency of the mass-sensitive element 112 communicating with the secondary channel 104.

FIGS. 8a-8f illustrate an exemplary fabrication process of a PM monitor 100 in accordance with embodiments of the invention. This process is provided by way of example and not limitation. The dimensions, materials, order of steps, and the like may be varied in different embodiments of the invention. The following example is presented to show fabrication techniques and processes implemented by the instant inventors to build a PM monitor 100 in accordance with the invention.

As shown, the PM monitor 100 was fabricated by bonding together three micromachined fused quartz wafers 800, 810, 814. The top quartz wafer 800 was used as a substrate for the microfluidic circuit 106 and the thermophoretic heater 206, necessitating later inversion of the wafer stack from the position shown in the Figures.

Referring now to FIG. 8a, the top quartz wafer 800 was fabricated by depositing a layer of undoped polysilicon 802 on the top quartz wafer 800, and lithographically patterning the undoped polysilicon layer 802 to define a thermophoretic heater 206. An approximately 5 μm undercut was created by a 20 minute etch in 5:1 Buffered Hydrofluoric Etch ("BHF").

Figure 8B:
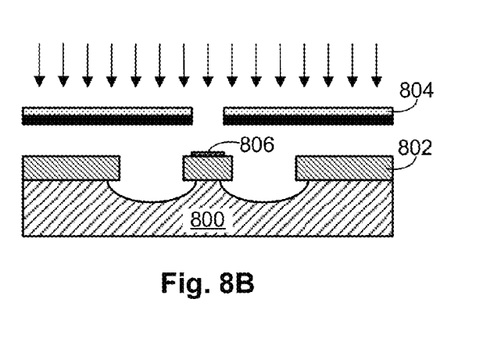
Figure 8C:
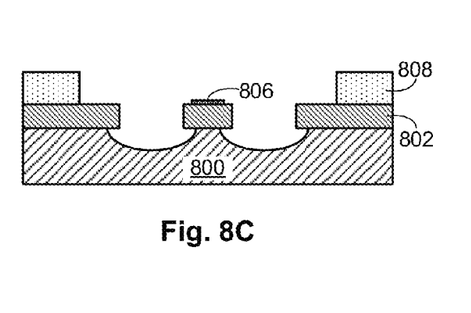
Figure 8D:
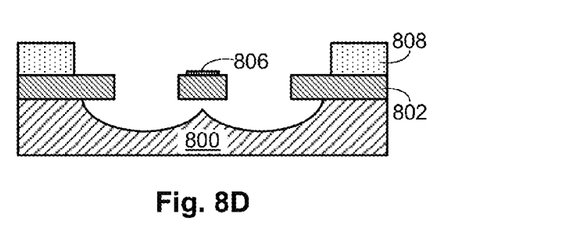

Referring now to FIG. 8b, a 100 nm layer of gold (Au) with a 5 nm chromium (Cr) adhesion layer 806 was then deposited via thermal evaporation through a shadow mask 804, ensuring only deposition of gold on polysilicon leads connected to the thermophoretic heater 206. As shown in FIG. 8c, a 200 μm layer of thick photodefinable resist 808 (for example, Michrochem SU-8 2150) was then deposited and photolithographically defined to form the microfluidic circuit 106. The thermophoretic heater 206 was subsequently released by a 10 minute etch in 49% hydrofluoric acid (HF), as shown in FIG. 8d. An additional 5 nm of gold was sputtered onto the thermophoretic heater 206 to reduce its resistivity to 5 Kohms.

Figure 8E:
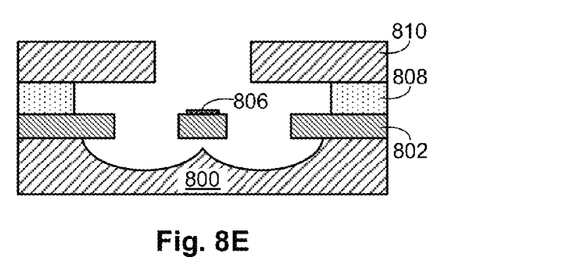

As shown in FIG. 8e, the middle quartz wafer 810 was fabricated to provide a cap for the microfluidic circuit 106, contain air inlet 204 and outlet 110 holes, and provide a cavity through which the mass-sensitive element 112 may be inserted into the microfluidic circuit 106. The air inlet 204 and outlet 110 holes and the cavity were created by laser machining and then annealing the wafer 810.

Figure 8F:
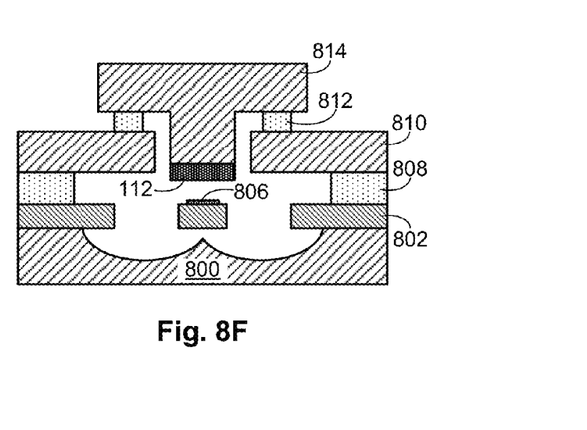

Referring now to FIG. 8f, the bottom wafer 814 provided a substrate for mounting the mass-sensitive element 112 and the conversion circuitry 120. 110 nm Cr/Au was deposited onto a gold wafer, and power and signal leads to the conversion circuitry 120 were photolithographically defined. A 50 μm thick layer of SU-8 812 was deposited and photolithographically patterned to form the seal 302 around the mass-sensitive element 112 and conversion circuitry 120. The power and RF connectors were soldered onto the bottom wafer 814. The mass-sensitive element 112 and conversion circuitry 120 were then bonded to the bottom wafer 814 with a rapidly drying adhesive, and wirebonded to the gold leads. All three wafers 800, 810, 814 were then aligned and bonded together using adhesive to form the final three-wafer stack.

In some embodiments, the materials and elements included in the fabrication process may facilitate identification of the particles collected. For example, in one embodiment, any or all of the structures and components of the PM monitor 100 may be fabricated using substantially transparent materials, such as glass or fused silica, to facilitate optical recognition and/or counting of the collected particles. An optical source and receiver may be used to provide speciation of particles contained in the air samples 100 or collected on the collection surface 208 of the mass-sensitive element 112, based on characteristic optical properties such as absorption or reflection.

In one embodiment, an optical beam may be directed from outside the ends of the microfluidic circuit 106. The optical beam may have a wavelength tunable to match the maximum attenuation of a particular gas of interest. Mirrors may be fabricated at the ends of the microfluidic circuit 106 to cause the optical beam to make multiple passes along its length, thereby providing a sensitive measurement of attenuation due to the presence of the gas of interest in the microfluidic circuit 106.

In certain embodiments, only materials used to form the microfluidic circuit 106 may be substantially transparent to electromagnetic radiation such as visible and/or infrared illumination, while materials used to form other structures and elements of the PM monitor 100 are not so limited. In one embodiment, the mass-sensitive element 112 may be used in conjunction with the transparent materials to perform photoacoustic analysis of the particles.

Photoacoustic analysis may involve shining pulses of swept-frequency optical illumination (i.e., infrared light) on the collected particles, causing the particles to absorb the light at certain frequencies and become heated. This may create a time-varying pressure in the gas above the mass-sensitive element 112 and collection surface 208. In embodiments where the mass-sensitive element 112 is a piezoelectric crystal or FBAR, this variance in pressure may be detected by the mass-sensitive element 112, which may produce a photoacoustic absorption spectrum from which the identity of the particles can be determined. Indeed, since the absorption spectrum of the pulsed illumination varies with the substance illuminated, the composition of the particles may be identified based on the photoacoustic spectrum produced by the mass-sensitive element 112.

The invention may be embodied in other specific forms without departing from its spirit or essential characteristics. The described examples are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. An apparatus for measuring concentrations of airborne particulate matter, the apparatus comprising:
    a primary channel to receive air samples from an external environment, the air samples comprising particles of varying sizes;
    a microfluidic circuit communicating with the primary channel, wherein particles having a size less than a threshold size are diverted around a bend into a secondary channel in communication with the primary channel, while remaining particles having a size larger than the threshold size and unable to make the bend continue through the primary channel; and
    a mass-sensitive element communicating with the secondary channel and comprising a collection surface to collect the particles having a size less than the threshold size, wherein a resonant frequency of the mass-sensitive element is reduced in proportion to the mass of the particles collected;
    wherein the secondary channel extends between first and second ends, the first and second ends both coupled to the primary channel having the mass-sensitive element communicating with the secondary channel between the first and second ends.

2. The apparatus of claim 1, further comprising an air pump communicating with the microfluidic circuit to create a pressure gradient to draw the air samples into the primary channel and through the microfluidic circuit.

3. The apparatus of claim 1, further comprising a deposition element to facilitate deposition of the particles onto the collection surface of the mass-sensitive element.

4. The apparatus of claim 3, wherein the deposition element comprises one of a thermophoretic element and an electrophoretic element.

5. The apparatus of claim 1, further comprising electric circuitry to convert a rate of change of the resonant frequency of the mass-sensitive element to a measured mass concentration.

6. The apparatus of claim 1, wherein the mass-sensitive element comprises a piezoelectric crystal.

7. The apparatus of claim 1, wherein the mass-sensitive element further comprises an electret to attract charged particles.

8. The apparatus of claim 1, further comprising a speciation element in communication with the microfluidic circuit to facilitate at least one of particle identification and quantification.

9. The apparatus of claim 1, wherein the speciation element utilizes one of optical speciation and photoacoustic speciation to identify the particles.

10. A method for measuring concentrations of airborne particulate matter, the method comprising:
    drawing air samples into a primary channel from an external environment, the air samples comprising particles of varying sizes;
    diverting particles having a size less than a threshold size around a bend into a secondary channel in communication with the primary channel;
    enabling remaining particles having a size larger than the threshold size and unable to make the bend to continue through the primary channel; and
    collecting the particles having a size less than the threshold size onto a mass-sensitive element communicating with the secondary channel, wherein a resonant frequency of the mass-sensitive element is reduced in proportion to the mass of the particles collected;
    wherein drawing the air samples into the primary channel comprises utilizing an air pump to create a pressure gradient between the external environment and the primary channel;
    wherein the method further comprises varying the speed of the air pump to vary the size of the particles contained within the air samples.

11. The method of claim 10, wherein collecting the particles further comprises utilizing one of thermophoretic and electrophoretic forces to attract the particles having a size less than a threshold size to a collection surface of the mass-sensitive element.

12. The method of claim 10, further comprising calculating a rate of change of the resonant frequency of the mass-sensitive element.

13. The method of claim 12, further comprising converting the rate of change of the resonant frequency of the mass-sensitive element to a measured mass concentration.

14. The method of claim 10, further comprising analyzing the particles to at least one of identify and quantify various particulate matter species.

15. The method of claim 14, wherein analyzing the particles comprises performing one of optical speciation and photoacoustic speciation to identify the various particulate matter species.

16. The method of claim 13, further comprising performing optical counting of the particles collected onto the mass-sensitive element and calculating the density of the collected particles from their measured mass concentration to provide particle speciation.

17. The apparatus of claim 1, further comprising first, second, and third quartz wafers, the mass-sensitive element being contained in the bottom wafer, the second wafer defining an inlet and an outlet of the primary channel, and the third wafer defining the microfluidic circuit.

18. The apparatus of claim 1 further comprising an air pump including first and second fans and a stator, the stator being positioned between the first and second fans and being fixed, the stator having an opposite chirality from the first and third fans.

* * * * *